(12) United States Patent
Tamez et al.

(10) Patent No.: US 11,123,219 B2
(45) Date of Patent: Sep. 21, 2021

(54) MOUTH APPLIANCE AND A METHOD TO IMPROVE BREATHING DURING SLEEP AND EXERCISE

(71) Applicants: Oscar Tamez, Georgetown, TX (US); JoAnn Tamez, Georgetown, TX (US)

(72) Inventors: Oscar Tamez, Georgetown, TX (US); JoAnn Tamez, Georgetown, TX (US)

(*) Notice: Subject to any disclaimer, the term of this patent is extended or adjusted under 35 U.S.C. 154(b) by 329 days.

(21) Appl. No.: 15/946,183

(22) Filed: Apr. 5, 2018

(65) Prior Publication Data
US 2019/0307599 A1   Oct. 10, 2019

(51) Int. Cl.
*A61F 5/56* (2006.01)
*A61F 5/58* (2006.01)

(52) U.S. Cl.
CPC ............... *A61F 5/566* (2013.01); *A61F 5/56* (2013.01); *A61F 5/58* (2013.01); *A61F 2005/563* (2013.01)

(58) Field of Classification Search
CPC .... A61F 5/56; A61F 5/566; A61F 5/58; A61F 2005/563; A63B 71/085; A61C 7/08; A61C 7/36; A61C 7/12; A61C 7/10; A61C 5/14; A61B 5/08; A61B 5/4818; A61B 5/0488; A61M 16/0488; A61M 16/049; A61M 16/0493
USPC .......................... 128/846, 848, 859, 861, 862
See application file for complete search history.

(56) References Cited

U.S. PATENT DOCUMENTS

| | | | | |
|---|---|---|---|---|
| 4,114,614 A | * | 9/1978 | Kesling | A63B 71/085 128/861 |
| 5,794,627 A | * | 8/1998 | Frantz | A61F 5/566 128/848 |
| 6,129,084 A | | 10/2000 | Bergersen | |
| 6,652,276 B2 | * | 11/2003 | Fischer | A61C 5/90 433/140 |
| 7,520,281 B1 | * | 4/2009 | Nahabedian | A61F 5/566 128/848 |
| 7,810,502 B1 | | 10/2010 | Nguyen et al. | |
| 9,545,331 B2 | | 1/2017 | Ingemarsson-Matzen | |
| 2004/0089310 A1 | | 5/2004 | Portnoy | |
| 2007/0235037 A1 | * | 10/2007 | Thornton | A61F 5/566 128/848 |

(Continued)

OTHER PUBLICATIONS

X.E. Cai and H. Shen, Apparent Activation Energies of the Non-Isothermal Degradation of EVA Co-polymer, 1999, Journal of Thermoanalysis and Calorimetry; vol. 55, pp. 67-76 (Year: 1999).*

*Primary Examiner* — Alireza Nia
*Assistant Examiner* — Daniel A Miller
(74) *Attorney, Agent, or Firm* — Maier & Maier, PLLC (57) ABSTRACT

A mouth appliance to promote nasal breathing and reduce or eliminate snoring and to help improve breathing during exercise. The mouth appliance includes upper and lower pieces that are hinged in the rear and conformed to fit the mouth and teeth of a wearer. The upper and lower mouth pieces come together to create a seal and promote nasal breathing. The frame of the mouth appliance may be formed from a hard or semi-hard material, and may be form-fitted to the mouth of a wearer to ensure both comfortable and effective use. The upper and lower pieces include a latching mechanism that allows for the mouth to be opened, closed, or semi-opened during wear and use of the appliance, and also allows for talking and drinking without removing the mouth appliance. The mouth piece can be worn at any time and provide protection of the teeth.

13 Claims, 6 Drawing Sheets

(56) References Cited

U.S. PATENT DOCUMENTS

| | | | |
|---|---|---|---|
| 2008/0099029 A1 | 5/2008 | Lamberg | |
| 2008/0135056 A1* | 6/2008 | Nelissen | A61F 5/566 128/848 |
| 2008/0216843 A1* | 9/2008 | Jiang | A61F 5/566 128/848 |
| 2010/0043805 A1 | 2/2010 | Kelly | |
| 2011/0017220 A1* | 1/2011 | Lindsay | A61F 5/566 128/848 |
| 2011/0195376 A1* | 8/2011 | Boyd, Sr. | A61C 7/36 433/140 |
| 2011/0226261 A1* | 9/2011 | Hernandez | A61F 5/566 128/848 |
| 2013/0098372 A1 | 4/2013 | Webster et al. | |
| 2014/0053852 A1* | 2/2014 | Thornton | B29B 13/02 128/862 |
| 2015/0216715 A1* | 8/2015 | Chung | A61F 5/566 128/848 |
| 2015/0258417 A1* | 9/2015 | Rodgers | A63B 71/081 128/861 |
| 2016/0338870 A1* | 11/2016 | Walton | A61F 5/56 |
| 2017/0312118 A1* | 11/2017 | De Heer | A61F 5/08 |
| 2018/0228644 A1* | 8/2018 | Shin | A61B 5/4818 |
| 2019/0021901 A1* | 1/2019 | LeBlanc | A61C 7/36 |

* cited by examiner

MOUTH APPLIANCE AND A METHOD TO IMPROVE BREATHING DURING SLEEP AND EXERCISE

BACKGROUND

With nasal breathing during sleeping, the tongue moves forward and high in the mouth to clear the back of the tongue/Posterior Airway Space (PAS), so allowing treatment of Upper Airway Resistance Syndrome (UARS), snoring, improvement of Obstructive Sleep Apnea (OSA), symptoms such as restless sleep, sleep talking, nightmares and thumb sucking. Also, the nasal breathing improves energy and fatigue, control of hypertension, diabetes and cardiovascular disease/heart disease accompanying better sleep. By promoting better nasal breathing and reducing/eliminating leak of air through the mouth, a patient gets better treatment of Continuous Positive Airway Pressure (CPAP) and better tolerance of CPAP. The benefits of CPAP are frequently lost by air leaking through the mouth, or, very commonly, a lack of desire for a user to wear a CPAP mask based on comfort or anxiety.

Further, reducing mouth breathing at night for children reduces cavities because the saliva of mouth has lubricating and antibacterial properties and the nasal breathing prevents dry mouth. It will also reduce morning bad breath and drooling. The mouth breathing may promote abnormal craniofacial growth for children, so the nasal breathing at night could be beneficial for normal craniofacial growth and reduce a child's chance of developing OSA because of posterior and narrow craniofacial structure. In orthodontics, promoting nasal breathing reduces the chances of orthodontic intervention failure, and by nasal breathing, grinding, clenching of teeth, and thumb sucking can be eliminated at night.

Also, better sleep has been proven to help Attention Deficit Disorder (ADD)/Attention Deficit Disorder Association (ADHD), Anxiety, Depression, Sensorineural issues, moodiness, acting out, or etc. Accordingly, all psychiatric illness can be improved with better sleep.

Additionally, best optimization of asthma and other lung/pulmonary issues begins with nasal breathing and the positive effects of Nitric Oxide. Also, bedwetting, failure to thrive/low percentile for height and weight, ADD/ADHD, acting out, sensory processing issues such as sensitivity to sounds, textures of food and clothing, thumb sucking can be improved with promoting nasal breathing during sleep. Furthermore, headaches/migraines, seizures and Tics could be improved with better sleep.

By breathing through our nose during exercise, people get 20% more oxygen because it may allow the nitric oxide produced in the nose and sinuses to efficiently get to the lungs, for vasodilation to occur in the arterioles and increase the surface area of the lungs for better oxygenation. Contrarily, by the mouth breathing, non-humidified air goes into the lungs, and it may cause airway spasm, exacerbation of asthma and reactive airway disease. There are various breathing skills for exercising, for example: (1) breathing in and out through the nose; (2) in through the nose and out through the mouth; (3) or hybrid exhalation (exhaling through the nose and mouth with mouth nearly closed), and an appliance which can be used for various ways of the breathing would be beneficial for an exerciser.

There are many mouth appliances to promote better sleep by advancing the jaw forward to open the PAS. However, such a conventional appliance does not allow a user to speak and drink while using the appliance. Also, there is no appliance that offers all forms of nasal and mouth breathing and its combination. There are appliances to protect the teeth from grinding, but those appliances cannot reduce the cause of grinding, which is the mouth breathing. There are sports appliances to protect the teeth for contact sports, to help clinching of teeth during the sports such as baseball and weight lifting, but they are not specifically to promote the nasal breathing, the mouth breathing or the combination. Therefore, it can be beneficial for the user if the appliance is designed to be used during nighttime rest as well as during exercise with the ability to speak and drink while using the appliance. However, the appliance can be worn at any time, as desired, and also act to protect the teeth of a wearer during any physical activity, such as exercise.

SUMMARY

Exemplary embodiments described herein generally relate to a mouth appliance and a method to improve breathing and sleeping, and, more specifically, to the mouth appliance and a method which promote nasal breathing and reduce or eliminate snoring.

Such a mouth appliance may include: an upper mouth piece; a lower mouth piece; a hinge connecting the upper mouth piece and the lower mouth piece; and a locking mechanism locking the upper mouth piece and the lower mouth piece. Also, in an exemplary embodiment, the upper mouth piece and the lower mouth piece is closed or opened incrementally by the locking mechanism.

BRIEF DESCRIPTION OF THE FIGURES

Advantages of embodiments of the present invention will be apparent from the following detailed description of the exemplary embodiments thereof, which description should be considered in conjunction with the accompanying drawings in which like numerals indicate like elements, in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

According to an exemplary embodiment, and referring generally to the Figures, various exemplary implementations of a mouth appliance may be disclosed. According to an exemplary embodiment, the mouth appliance may be designed to improve breathing and sleeping. In particular, the mouth appliance may be designed to promote nasal breathing and to reduce snoring.

According to an exemplary embodiment, a mouth appliance may be designed to promote nasal breathing and reduce/eliminate mouth breathing. In an exemplary embodiment, the mouth appliance may be a multifaceted appliance that may be used day and night, at rest, and during exercise as well as sleep. For example, when the mouth appliance is used at nighttime, unlike conventional oral devices for snoring and sleep that promote nasal breathing, the appliance may promote complete mouth closure at night, but the user of the mouth appliance may also open mouth to talk, or to drink without removing the appliance. Also, the appliance may allow the hybrid (mouth and nasal) breathing for those who cannot tolerate complete mouth breathing because of severe nasal obstruction.

According to an exemplary embodiment, the mouth appliance may be "unlock" for speaking etc., for example, to converse with spouse while in bed. Also, in an exemplary embodiment, for the best nasal breathing or for some jaw advancement to open the posterior airway space, the mouth appliance may provide a tension free experience of mouth closure without clenching or biting the appliance. For example, the mouth appliance may have an easily accessible locking and unlocking mechanism such as latch or a simple click mechanism (that may consist of a magnet, latch, spring, etc. or combination of these as desired) to keep closed and open with simple bite of the appliance or sliding of a lower jaw. Also, a vertical height between the upper teeth and the lower teeth with the appliance may provide more room for tongue to increase posterior airway space.

According to an exemplary embodiment, the mouth appliance may advance a mandible in order to open the posterior airway space, which is for better sleep. In an exemplary embodiment, the mouth appliance may be in one size fits all. Also, in an exemplary embodiment, in the mouth appliance, the piece of the appliance may slide to click in place by, for example, one milli-meter (mm) increments with no more than 3 advancement points to reduce the tension which may cause Temporamandibular Joint (TMJ) issues, teeth movement or tooth soreness.

Figure 1:
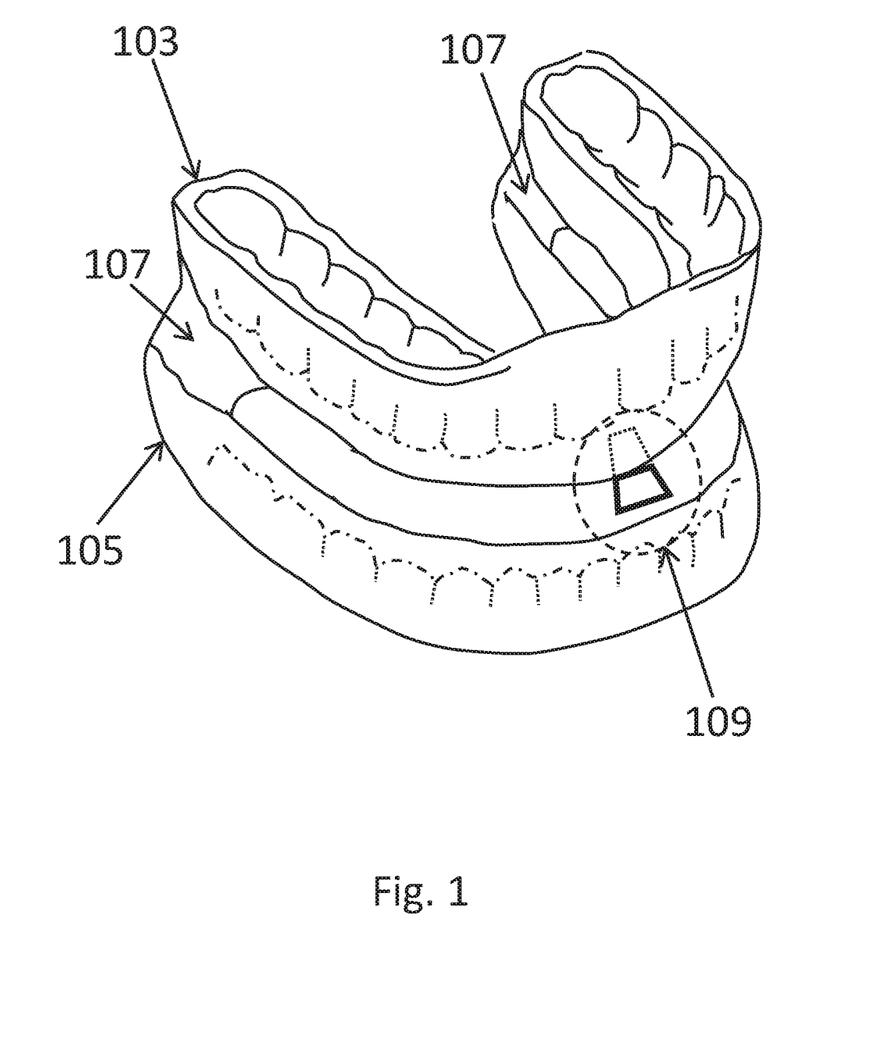
FIG. 1 is an exemplary embodiment of a latch mechanism of a mouth appliance.

Turning now to exemplary FIG. 1, FIG. 1 shows a mouth appliance. According to an exemplary embodiment, the mouth appliance may include an upper mouth piece 103 and a lower mouth piece 105, and the upper and lower mouth pieces (103 and 105) may be connected via a hinge 107 in the rear. In an exemplary embodiment, the mouth appliance may be conformed to the teeth with a softer standard impression material. The upper and lower mouth pieces (103 and 105) may come together to create a seal and promote nasal breathing. The frame of the mouth appliance may be made with a hard or semi-hard material such as plastic, silastic, silicone, acrylic, latex or any other soft material which has a standard FDA approved and is BPA (bisphenol) free, and can either be warmed/heated in water to fit the individual teeth and bite. Also, in an exemplary embodiment, the hinge 107 of the mouth appliance may be of a thinner version of the frame material or other material, for example, the hinge 107 may be made of a flexible and soft piece of plastic that may connect the upper and lower mouth pieces (103 and 105) and may allow comfortable wear with easy vertical and horizontal movements of the jaw. Further, it may be appreciated that the vertical and horizontal movements may be limited to a desired or predetermined range so as to provide effective use of the mouth appliance.

According to an exemplary embodiment, the mouth appliance may have an added attachment (not shown in the drawing) at night, which is provided between the front teeth and lips to create a better seal. Also, in an exemplary embodiment, the mouth appliance may have an attached gripping element or handle (not shown in the drawing) that allows a user to grab and pull out appliance, and vertical and lateral movements of the lower jaw may help for better comfort of the mouth appliance. According to another exemplary embodiment, the mouth appliance may have an attachment or tape (not shown in the drawing) that in conjunction (attached or separated) may dilate the nostrils directly, for example, like the breathe rite strips or indirectly by pulling on the nose. Also, in an exemplary embodiment, the mouth appliance may have an attachment or tape (not shown in the drawing) around the chin to further support a closed mouth. Further, the appliance may be such that, when worn, it protects the wearer's teeth, for example during exercise or other activities.

According to an exemplary embodiment, the mouth appliance may be used during day time with exercise or rest: Unlike conventional oral devices for exercise and at rest that promote nasal breathing, as described above, the mouth appliance may enable the complete mouth closure as well as may open the mouth to talk or drink as needs without removing the appliance. Also, in an exemplary embodiment, the mouth appliance may allow the hybrid (mouth and nasal) breathing for those who cannot tolerate complete mouth breathing because of severe nasal obstruction or who prefer hybrid (nasal and mouth breathing) breathing over nasal only or "belly" breathing. (Nasal breathing only, while exercising, is termed abdominal or "belly".) Users of the mouth appliance may even be able to breathe only through their nose with the mouth appliance as desired. Accordingly, the mouth appliance may be suited to accommodate nasal breathing only, mouth breathing only, or hybrid mouth and nasal breathing. Also, in an exemplary embodiment, the unlocking mechanism 109 may allow hybrid breathing, and users may easily open mouth wide to breathe only though the mouth if so desired. According to an exemplary embodiment, with simple unlocking, a small separation of upper and lower mouth pieces (103 and 105) may allow the hybrid breathing during exercise. Also, the increased height by the upper and lower mouth pieces (103) may allow more room for tongue increasing Posterior Airway Space (PAS).

Turning now to exemplary FIG. 2A-2D, FIG. 2A shows an exemplary embodiment of a locking or unlocking mechanism of a mouth appliance. According to an exemplary embodiment, a latching mechanism 109 may be used in a mouth appliance, and any locking mechanism which allows for a complete shut application and a semi shut application may be applicable. The locking mechanism 109 may include a latch 213 coupled to one of the mouth pieces, engageable with slots 205, 207 defined in an occlusal surface 216 of the other of the mouthpieces. A plunger 214 may be movable in a front-rear direction 210 parallel to the occlusal surface 216 of the mouthpiece in which the slots and plunger are disposed. The plunger may be biased by a resilient element such as a spring 203 so as to exert a force on the latch 213, thereby maintaining the latch 213 engaged in one of slots 205, 207. Also, in an exemplary embodiment, materials for the locking mechanism 109 may be of the same or a more rigid material as the frame of the mouth appliance. For example, the locking mechanism 109 materials may be such that they are not altered, deformed, or otherwise changed when the mouth appliance is warmed to mold to the teeth of a wearer. According to an exemplary embodiment, when the mouth appliance is unlatched, the mouth appliance may allow talking and drinking without having to remove the entire appliance. Also, in an exemplary embodiment, the first slot 207 of the locking mechanism 109 may allow a gap between the upper mouth piece 103 and lower mouth piece 105 so that mouth and nasal breathing can occur simultaneously or separately. Accordingly, from the "open" position, closing the jaws may allow the locking mechanism 109 to go to the slot (the first notch) 207 for the "hybrid breathing" which allows the user to be able to breathe through their nose and mouth.

Figure 2A:
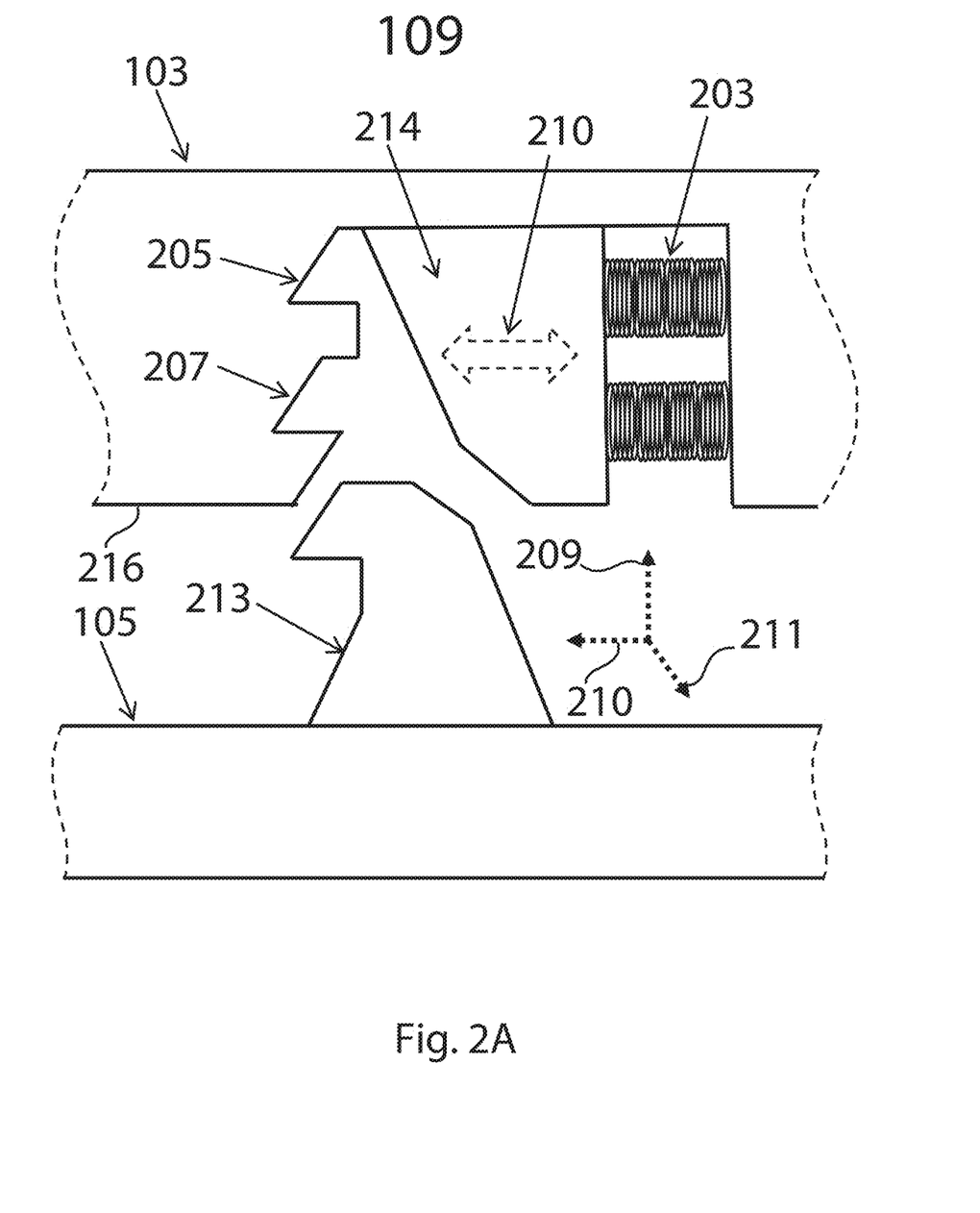
FIG. 2A is a latch mechanism of a mouth appliance according to an exemplary embodiment.
Figure 2B:
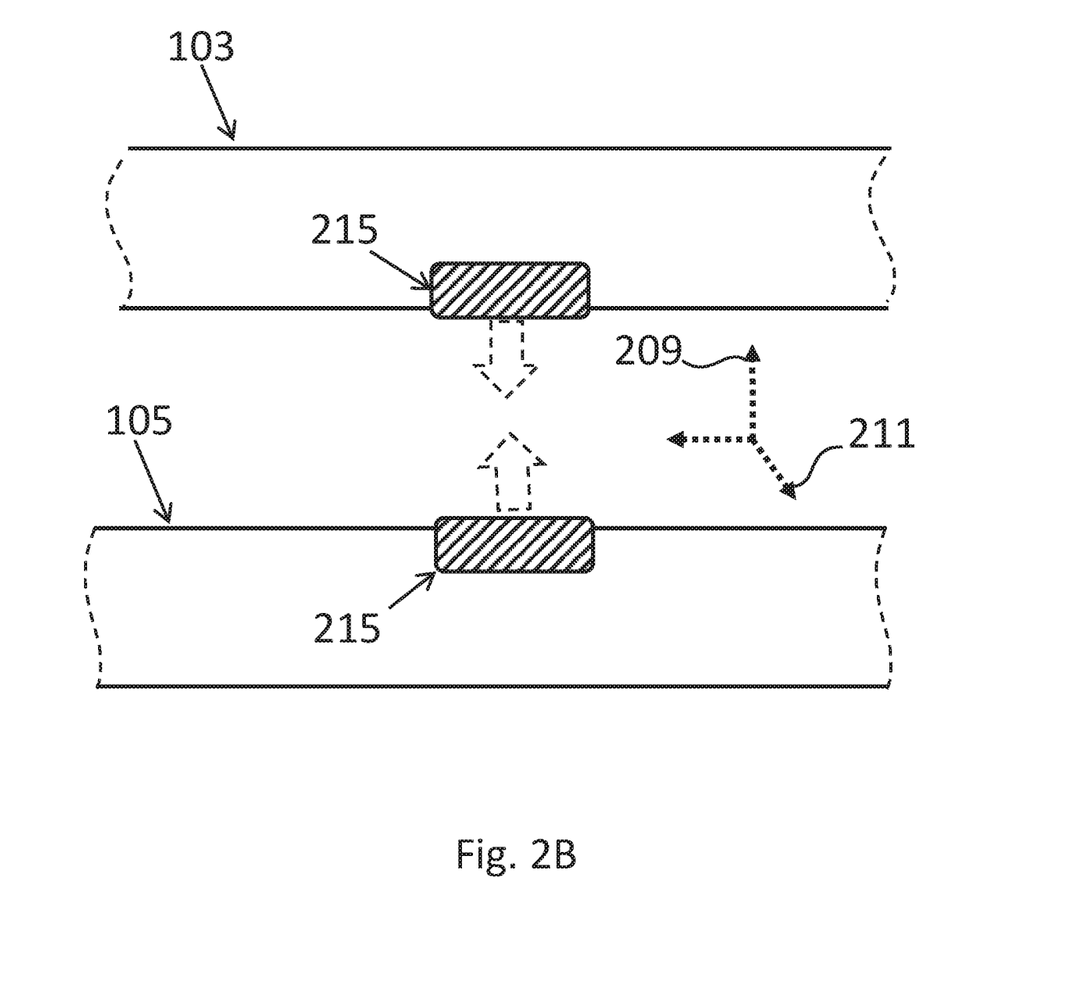
FIG. 2B is a latch mechanism of a mouth appliance which uses magnets according to an exemplary embodiment.

Referring still to FIG. 2A, in an exemplary embodiment, the second notch 205 may allow for complete nasal only breathing. Also, in an exemplary embodiment, the hinge 107 may not only allow opening and closing of the mouth (vertical movements 209), but also may allow side movements 211 of the upper and lower pieces (103 and 105) of the mouth appliance. According to an exemplary embodiment, the lateral movement 211 may be to move the latch 213 of the mouth appliance out of the socket of the locking mechanism 109 in order to open the mouth. Accordingly, the movement of the lower jaw may allow the disengagement (the fully "open" position) of the latch as well as the fully closed "nasal breathing with the slot (the second notch) 205 position. This can provide a wearer of the mouth appliance to adjust, lock, and unlock the device without the use of their hands. Thus, the mouth appliance may be easier to use and more sanitary than traditional oral appliances. Further, the lateral movement 211 may be for a further positive attribute of a desirable oral appliance. Again, the locking mechanism 109 provided in FIG. 2 is merely one example of a locking or unlocking mechanism, and any mechanical structure which allows the complete locking or shutting and/or a semi-shut application may be applicable.

Figure 2C:
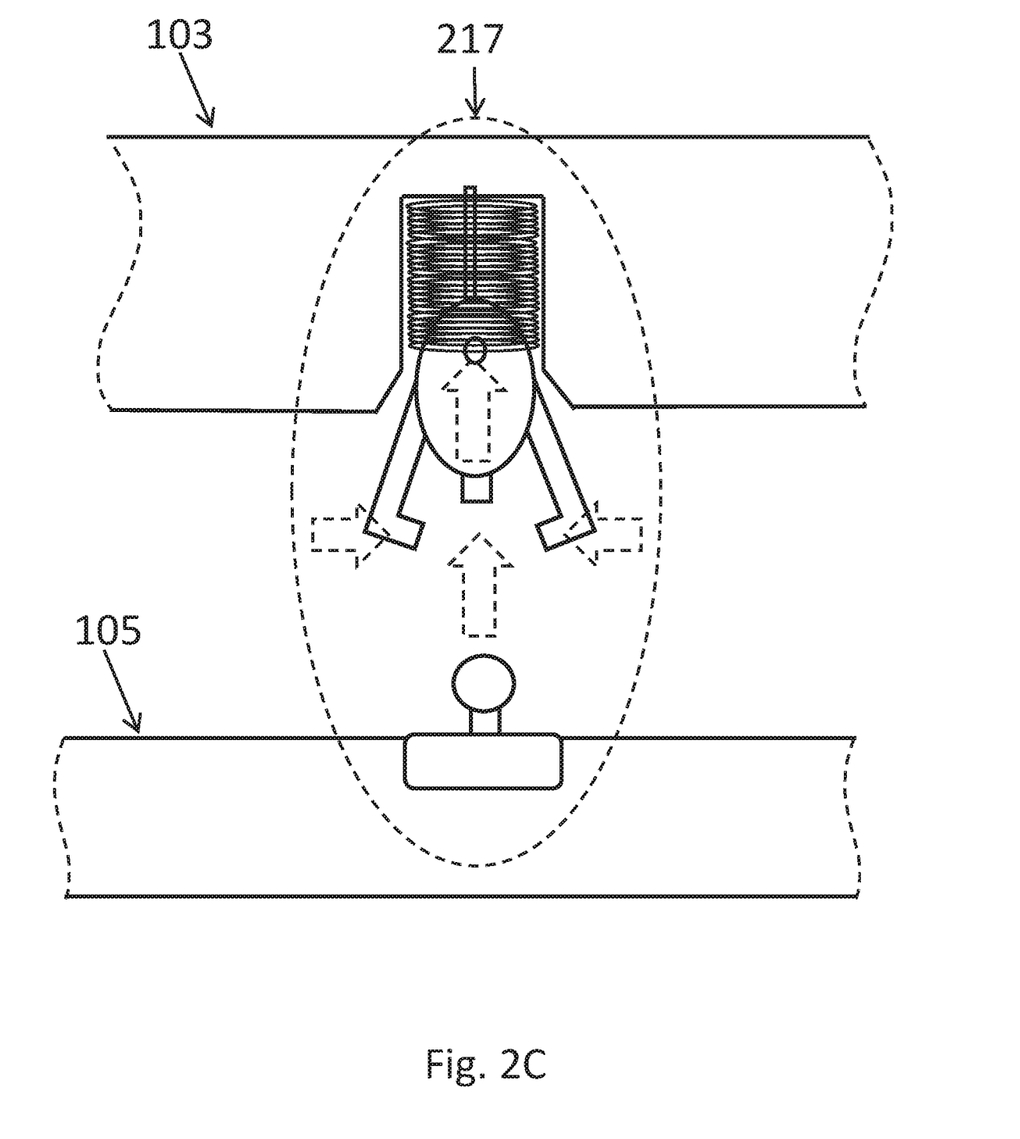
FIG. 2C is a latch mechanism of a mouth appliance which uses a pressure latch according to an exemplary embodiment.
Figure 2D:
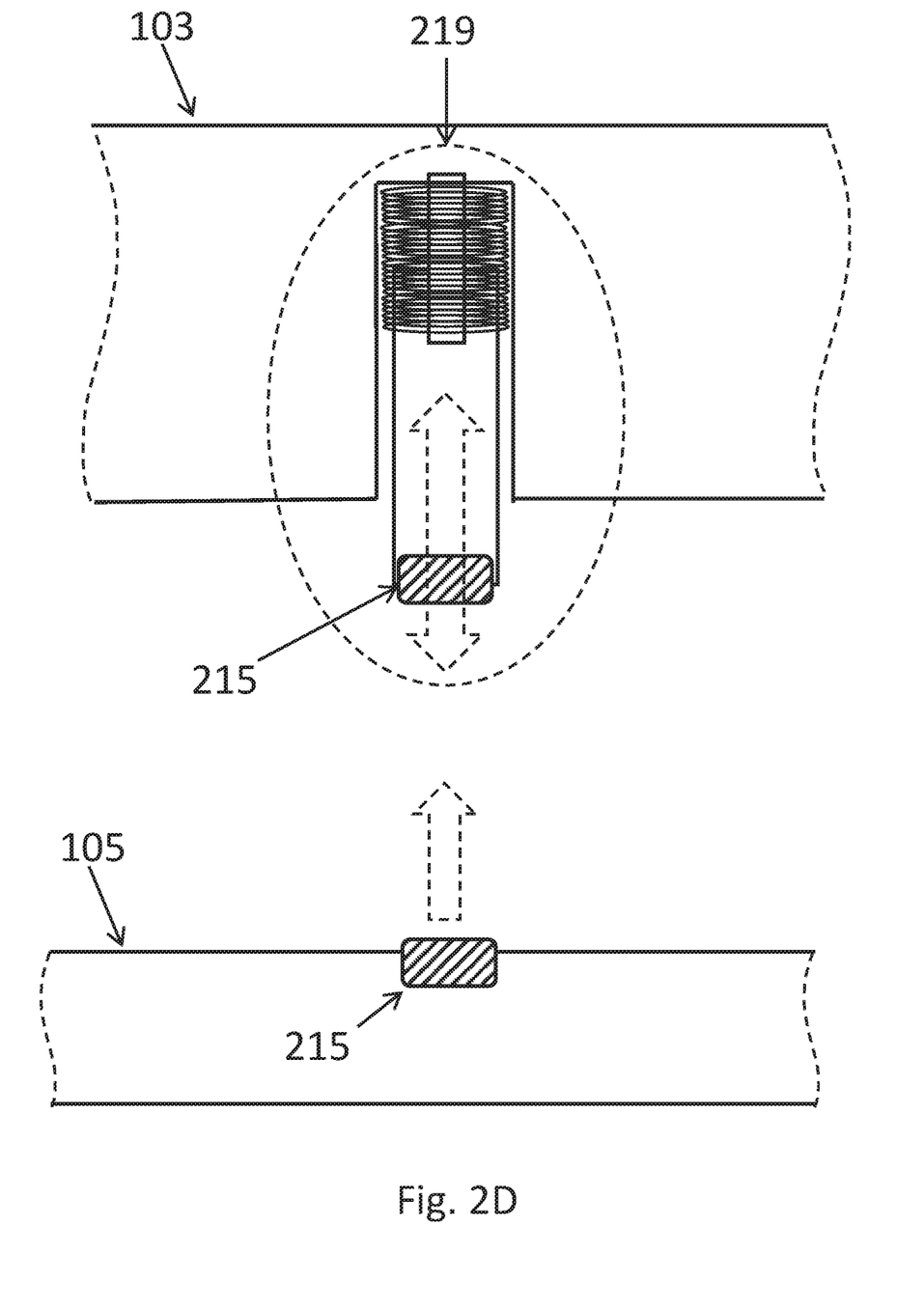
FIG. 2D is a latch mechanism of a mouth appliance which uses a retractable mechanism according to an exemplary embodiment.

In some other exemplary embodiments, it may be appreciated that the locking mechanism 109 may include micro springs 203, magnets 215 (shown in FIGS. 2B and 2D) or a simple snap (not shown in the drawing) on a latch that may or may not utilize a person's hand to adjust to get complete and near complete the closure of the mouth. Also, as shown in FIG. 2C, in another exemplary embodiment, a locking or unlocking mechanism may use a pressure latch 217 which may be closed and released with simple biting down. Further, as shown in FIG. 2D, according to another exemplary embodiment, the mechanism of a retractable pens may be applied to a locking or unlocking mechanism. In an exemplary embodiment, a spring-loaded retractable mechanism 219 which retracts and is integral to the upper or lower mouth pieces (103 or 105) may be connected other mouth pieces (105 or 103) via magnets 215. According to an exemplary embodiment, when the retractable mechanism 219 is pushed to open, the magnets 215 may allow for continued connecting of the upper and lower mouth pieces (103 and 105), and thus, it may enable the hybrid breathing. Other types of hinges and locking mechanisms, formed of the same material as locking mechanism 109 described herein, may be utilized in some exemplary embodiments.

For example, multiple locking mechanisms may be utilized for different types of fitments or to provide different levels of jaw mobility. The use of springs 203 of varying tension may be utilized to create ease of jaw movement or restrict jaw movement to more deliberate or desired movements. For example, a spring system that traverses upper and/or lower portions of the appliance could be utilized to provide locking capabilities. Also, locking mechanisms could be located laterally in the appliance, for example with spring elements located laterally there on. Further, it may be appreciated that one or more locking mechanisms or latch may be mounted on an interior portion of the mouth appliance so as to make it tongue actuated or manipulatable.

Figure 3:
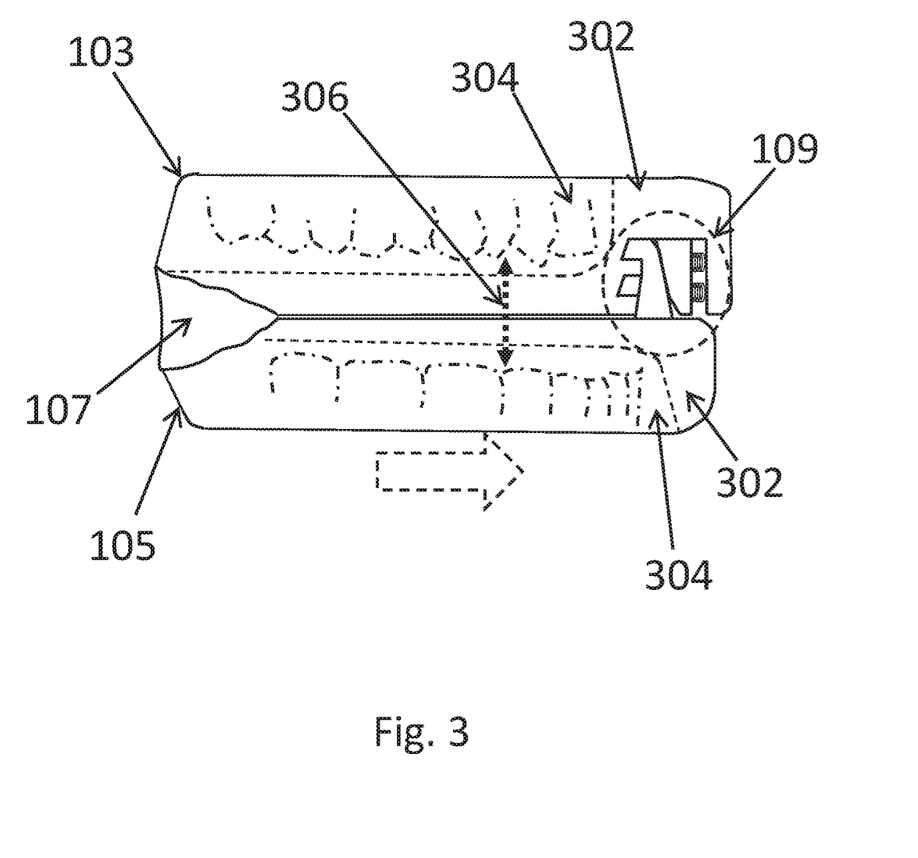
FIG. 3 is a lateral view of a mouth appliance according to an exemplary embodiment.

Turning now to exemplary FIG. 3, FIG. 3 may show a lateral view of a mouth appliance showing slight advancement of the jaw forward, which can allow for the opening of the back of the throat facilitating better breathing. According to an exemplary embodiment, users' teeth may be put in a standard FDA approved plastic moldable tray 304 of the mouth appliance, which may mold to the teeth when warmed, and the frame 302 of the mouth appliance may be made with a harder material not to be distorted. Also, in an exemplary embodiment, the frame 302 of the mouth appliance may be made of harder plastic, acrylic or other material, and may create a vertical height 306 of a few millimeters which may allow the tension free use of the mouth appliance. Because of the vertical height 306, users may not need to bite down during use the mouth appliance without undue pressure on teeth or temporal mandibular joint. Accordingly, the vertical height addition 306 may cause better breathing by allowing more space for the tongue in the mouth to increase Posterior Airway Space (PAS).

Referring still to FIG. 3, according to an exemplary embodiment, the lower piece 105 of the mouth appliance may cause the lower jaw to be advanced a few millimeter (mm) more than the upper teeth over the upper piece 105 so that the Posterior Airway Space (PAS) may have proper opening for better breathing during use. Also, it may prevent the tongue from falling back and obstructing the airway. In an exemplary embodiment, the mandibular advancement may come fitted, for example, at about 2-3 mm advancement, and may come in different advancement sizes (with an about 1 mm increment). Also, in an exemplary embodiment, the mandibular advancement may occur only when the locking mechanism 109 is engaged through the flexibility of the hinge 107 which may be made of a flexible and soft piece of plastic. In an exemplary embodiment, the locking mechanism 109 of the mouth appliance may be in the front/anterior of the appliance. There could be various options for closing of the mouth appliance as described above.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art (for example, features associated with certain configurations of the invention may instead be associated with any other configurations of the invention, as desired).

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. An apparatus for a mouth appliance comprising:
an upper mouth piece;
a lower mouth piece;
a hinge connecting the upper mouth piece and the lower mouth piece; and
a locking mechanism locking the upper mouth piece and the lower mouth piece, wherein the upper mouth piece and the lower mouth piece is closed or opened incrementally by the locking mechanism;
wherein the locking mechanism is adjustable between a first locked configuration and a second locked configuration by a movement of the upper mouth piece relative to the lower mouth piece;
wherein, in the first locked configuration, a vertical gap exists between the upper mouth piece and the lower mouth piece;
wherein, in the second locked configuration, no vertical gap exists between the upper mouth piece and the lower mouth piece;
wherein the locking mechanism includes a latch, at least two slots, and a movable plunger, the at least two slots and plunger being formed in an occlusal surface of one of the upper mouth piece and the lower mouth piece and the latch being coupled to the occlusal surface of the other of the upper mouth piece and the lower mouth piece;
wherein, in a locked configuration, the latch engages a slot of the at least two slots, and the plunger exerts a force against the latch in a front-and-rear horizontal direction, the front-and-rear horizontal direction being parallel to the occlusal surface of the upper mouth piece and the lower mouth piece, a front of the mouth appliance being an incisor-engaging region of the mouth appliance and a rear of the mouth appliance being opposite the front;
wherein the locking mechanism is provided at the incisor-engaging region of the mouth appliance and is configured to be located anteriorly, in the front-and-rear direction, of a user's teeth when the mouth appliance is worn.

2. The apparatus of claim 1, wherein the hinge is provided at the rear portion of the mouth appliance.

3. The apparatus of claim 1, wherein each of the upper mouth piece and the lower mouth piece comprising:
a frame made of at least one of a hard material and a semi-hard material; and
a tray made of a soft material.

4. The apparatus of claim 3, wherein the locking mechanism is made of at least one of the same material of the frame and a more rigid material than the frame.

5. The apparatus of claim 3, wherein at least one of the frame and the tray is molded or custom fit to teeth when warmed or heated in water.

6. The apparatus of claim 3, wherein the hard material and semi-hard material is at least one of a plastic, a silastic, a silicone, an acrylic, and a latex.

7. The apparatus of claim 1, wherein the locking mechanism includes a resilient element.

8. The apparatus of claim 1, wherein the hinge is made of a flexible and soft plastic.

9. The apparatus of claim 1, wherein the lower mouth piece is configured to advance, in a forward movement, a lower jaw relative to the upper teeth in the upper mouth piece when the lower mouth piece and the upper mouth piece are closed.

10. The apparatus of claim 1, wherein the locking mechanism is lockable by a biting action of a user in a vertical movement.

11. The apparatus of claim 9, wherein the forward movement is within three increments, and one increment is one milli-meter.

12. The apparatus of claim 1, wherein the latch is engageable with a first slot of the at least two slots defined in the upper mouth piece and with a second slot of the at least two slots defined in the upper mouthpiece;
when the latch is engaged with the first slot, a vertical gap exists between the lower mouth piece and the upper mouth piece;
when the latch is engaged with the second slot, the lower mouth piece and the upper mouth piece are closed without the vertical gap between the lower mouth piece and the upper mouth piece; and
when the latch is engaged with the first slot or the second slot, the resilient element exerts a force on the latch in the direction of the slot.

13. The apparatus of claim 1, wherein the apparatus is configured to increase a vertical height between upper teeth and lower teeth to enlarge a mouth space for a tongue increasing Posterior Airway Space (PAS).

* * * * *